United States Patent
Isager et al.

(12) 
(10) Patent No.: US 6,190,686 B1
(45) Date of Patent: Feb. 20, 2001

(54) WATER DISPERSIBLE COMPOSITIONS CONTAINING NATURAL HYDROPHOBIC PIGMENT, METHOD OF PREPARING SAME AND THEIR USE

(75) Inventors: Per Pihlmann Isager, Milwaukee, WI (US); Marianne Winning, Kokkedal (DK)

(73) Assignee: CHR. Hansen A/S, Hoersholm (DK)

( * ) Notice: Under 35 U.S.C. 154(b), the term of this patent shall be extended for 0 days.

(21) Appl. No.: 09/101,456

(22) PCT Filed: Jan. 14, 1997

(86) PCT No.: PCT/DK97/00015
§ 371 Date: Sep. 17, 1998
§ 102(e) Date: Sep. 17, 1998

(87) PCT Pub. No.: WO97/26802
PCT Pub. Date: Jul. 31, 1997

(30) Foreign Application Priority Data

Jan. 22, 1996 (EP) .................................. 96 610 003

(51) Int. Cl.[7] ............................ A61K 47/00; A61K 9/68; A61K 9/28; A23K 1/165; A23K 1/17
(52) U.S. Cl. .......................... 424/439; 424/440; 424/441; 424/442
(58) Field of Search .................................... 424/442, 441, 424/440, 439

(56) References Cited

FOREIGN PATENT DOCUMENTS

| 28 20 981 | 4/1979 | (DE) . |
| 0 498 824 | 8/1992 | (EP) . |
| 91/06292 | 5/1991 | (WO) . |
| 92/11002 | 7/1992 | (WO) . |
| 93/04598 * | 3/1993 | (WO) .............................. A23L/1/303 |

OTHER PUBLICATIONS

Hendry et al., "Natural Food Colorants", *Blackie Academic & Professional*, pp. 169–201, (1991).

* cited by examiner

*Primary Examiner*—Kimberly Jordan
(74) *Attorney, Agent, or Firm*—Foley & Lardner

(57) ABSTRACT

A ready-to-use water dispersible pigment composition containing at least 5% by weight of water is provided. The composition comprises a stable dispersion of a water-insoluble and/or hydrophobic natural pigment such as a carotenoid, curcumin, a porphyrin pigment or vegetables carbon black in the form of bodies of an average size which is at the most 10 $\mu$m is provided. The pigment bodies are dispersed without the use of a surface active substance in an aqueous phase comprising a hydrocolloid. The natural pigment in compositions which are useful for coloring of food products and pharmaceuticals do not migrate in the products. The compositions are useful in coating compositions for tablets and dragees.

20 Claims, No Drawings

WATER DISPERSIBLE COMPOSITIONS CONTAINING NATURAL HYDROPHOBIC PIGMENT, METHOD OF PREPARING SAME AND THEIR USE

This application is a 371 of PCT/DK97/00015, filed Jan. 14, 1997.

FIELD OF INVENTION

The present invention provides ready-to-use water dispersible compositions containing natural hydrophobic pigments, which compositions are in paste or liquid form and are useful for the colouring of edible products and pharmaceutical products.

TECHNICAL BACKGROUND AND PRIOR ART

Colouring agents are commonly used as additives in the manufacturing of food products and pharmaceuticals. A wide range of such colouring agents are commercially available making it possible when a particular colour tone is desired to select a single agent having the desired colour or a mixture of colours which in an appropriate combination impart the desired colour to the product.

The commercial colouring agents can be synthetic substances which are also normally referred to as dyes or azodyes, or the agents can be pigments of natural origin, e.g. in the form of plant material containing the pigment or as more or less purified pigments extracted from plants, animals or microorganisms.

Occasionally, food grade or pharmaceutically acceptable colouring agents are provided in the form of synthetic or artificial substances having the same chemical composition as naturally occurring pigments. This type of colouring agents are also referred to in the art as "nature identical" colours. However, in the present context the term "natural pigment" is used exclusively to designate pigments which are derived from a natural source.

Food grade or pharmaceutically acceptable natural pigments can be water soluble or they can be essentially water-insoluble or sparingly soluble in water, including hydrophobic pigments. A water soluble natural pigment as such can therefore only be used for colouring a product having an aqueous phase during and/or after manufacturing. Similarly, the use of a hydrophobic natural pigment as such requires that the product to be coloured has a lipid phase in which the pigment is soluble. Certain hydrophobic natural pigments such as curcumin are insoluble in water at neutral pH or below but soluble in alkaline aqueous media.

However, it may be desirable to obtain the colour tone of a particular water-insoluble and/or hydrophobic natural pigment or a mixture of such pigments in a food product or a pharmaceutical product which does not comprise a phase in which the pigment is readily soluble. There is therefore an industrial need for colouring agents containing water-insoluble and/or hydrophobic natural pigments in the form of water-miscible compositions.

In EP-B1-0 498 824 is disclosed a process for preparing a hydrophobic/aerophilic solid, including a natural colourant, in the form of a water dispersible microencapsulated powder resulting from spray drying a suspension of the solid.

Commercial water dispersible preparations of hydrophobic and/or water insoluble natural pigments such as turmeric are e.g. available from Overseal Foods Ltd, Derbyshire, England under the trade name miChroma™. These products are provided as suspensions in propylene glycol and glucose syrup and the manufacturer states in data sheets that the products will stain clothing and skin. This manufacturer also provides hydrophobic, water dispersible colouring agents containing lutein, natural carotene or paprika in the form of oil in water emulsions which are rendered water dispersible by addition of emulsifiers (Em-Seal™ products).

In the pharmaceutical industry and the food industry colouring agents are used widely for the colouring of sugar coatings of e.g. sugar confectioneries, dragees, tablets, pills, gums and granulates. Presently, most colouring agents available for this purpose are based on synthetic dyes, e.g. in the form of food grade lakes which are pigments formed by precipitation and absorption of a dye on an insoluble base or substrate, such as alumina hydrate. A wide range of coating compositions comprising such lakes are available. Propylene glycol-based dispersions are presently commonly used to incorporate such dyes into solutions used for film-coating of pharmaceutical tablets. It is recognized in the art that propylene glycol has a negative effect on both the processing time and physical properties of the film.

In DE 2 820 981 is disclosed an edible, water-insoluble powder for coating pharmaceutical tablets, consisting of cellulose or starch or derivatives hereof which is coloured with a natural pigment such as curcumin, annatto or grape skin extract.

WO 92/11002 discloses a film-forming composition for use in coating tablets and capsules, consisting of powdered pigment particles, a film-forming, water soluble or water dispersible, edible polymer and about 1–30% by weight of water. This composition is described as a wet powder blend and it is manufactured by blending the dry ingredient followed by the addition of water by spraying it onto the blend.

A well-known problem associated with the use of water soluble or dispersible compositions of colouring agents is the tendency of such agents to migrate from one compartment of a food product or a pharmaceutical product to another where the colouring is undesired. This phenomenon is also referred to as "bleeding".

It is therefore particularly desirable to have water soluble or dispersible natural pigment preparations which do not migrate during manufacturing or within the finished product during storage and handling, or come off when handled.

Other problems or shortages associated with known water-miscible natural colouring agents are low stability against light, heat, catalyst and oxygen generated changes of the colour hue and an unsatisfactory covering ability when used for coating purposes.

Thus, it is apparent that non-powdered, water dispersible colouring compositions containing water-insoluble and/or hydrophobic natural pigments, which are based on aqueous dispersions of the pigment without potentially undesirable additives including surface active substances or propylene glycol, which are more stable to degradation than known products, which are suitable for manufacturing of food products as well as pharmaceutical products, which do not migrate and which are not associated with the above problems have hitherto not been available to the industry.

The advantages obtained with the colouring agents of the present invention include:

their use give no dusting problems as it is the case with powdered products, their manufacturing does not include a drying step which implies that the production costs are lower and that the pigments are not damaged by heat and oxygen, they can be provided with a water content and a consistency which is adapted to the particular field of use, e.g. ranging from concentrated pastes to low viscosity products, they do not give rise to migration problems, they do not contain undesirable additives, they possess increased dosage performance, they possess increased chemical stability they confer desirable cloudiness or reflection to otherwise clear media.

SUMMARY OF THE INVENTION

Accordingly, the invention pertains in one aspect to a ready-to-use water dispersible pigment composition comprising a dispersion of a water-insoluble and/or hydrophobic natural pigment in the form of bodies of an average size which is at the most 10 µm, said bodies being dispersed in the absence of a surface active substance in an aqueous phase comprising a hydrocolloid in an amount of at least 1% by weight of the pigment, the composition containing at least 5% by weight of water.

In further aspects the invention relates to the use of such a composition in the manufacturing of an edible product whereby the composition is dispersed in the aqueous phase of said food product, including its use in the manufacturing of an edible product comprising multiple, separated compartments whereby the composition is dispersed in one or more selected compartments, the composition in one compartment essentially not migrating to other compartment.

In a still further aspect, the invention relates to the use of the above composition in the manufacturing of a pharmaceutical product.

Still further objectives of the invention are to provide an edible product or a pharmaceutical product comprising the above composition and a method of preparing a ready-to-use water dispersible pigment composition, said method comprising preparing a dispersion of a water-insoluble and/or hydrophobic natural pigment by comminuting the pigment in the absence of an emulsifying agent in an aqueous phase containing a hydrocolloid in an amount of at least 1% by weight of the pigment to obtain a dispersion containing the pigment in the form of bodies having an average size of at the most 10 µm, the composition containing at least 5% by weight of water.

DETAILED DISCLOSURE OF THE INVENTION

The ready-to-use composition according to the invention comprises a dispersion of a water-insoluble and/or hydrophobic natural pigment. As used herein the term "water-insoluble and/or hydrophobic" indicates that the pigment in the amounts used herein is water-insoluble or sparingly soluble in water in that the pigment will occur as a separate phase in aqueous media and/or has such a high degree of hydrophobicity that it can not be homogenously dispersed or suspended in water without the use of considerable shear stress and/or addition of surface active substances such as emulsifying agents. Most of such pigments will be soluble in lipid substances. Hydrophobic compounds may also be aerophilic.

In this context, the term "surface active substance" is used interchangeably with the term "surfactant" and "tenside" and it includes compounds which are generally referred to as anionic, cationic, non-ionic, amphoteric and zwitterionic surfactants. A review of such surface active substances is e.g. given by I Smith, Blackie Academic & Professional, 1991, 169–201. As used herein the term "surface active substance" does not include hydrocolloids as mentioned below. It is to be understood, that the expression "in the absence of surface active substances" does not exclude the presence of a surfactant in minor amounts which substantially does not impart surface activity.

The natural pigment can be any food grade or pharmaceutically acceptable water-insoluble and/or hydrophobic colouring matter derived from a natural source. Thus, the pigment may either be in a substantially pure form or it may be contained in the material where it occurs naturally such as a plant or animal material, optionally in combination with a food grade and/or pharmaceutically acceptable carrier. The most widely used natural hydrophobic pigments include carotenoids, curcumin, porphyrin pigments including chlorophyll, and vegetable carbon black.

Carotenoids which have yellow, orange or red colours occurs widely in nature and important sources are plants including grasses, the annatto tree, citrus species, *Capsicum annum*, *Crocus sativus* flowers and marigold flowers, marine algae, yeast and some animals. Carotenoids can be divided into the following classes: carotenoid hydrocarbons, xanthophylls and apocarotenoids. Typical examples of carotenoids include bixin, β-carotene, apocarotenals, canthaxanthin, saffron, crocin, capsanthin and capsorubin occurring in paprika oleoresin, lutein, astaxanthin, rubixanthin, violaxanthin, rhodoxanthin, lycopene and derivatives hereof.

Further water-insoluble and/or hydrophobic natural pigments which are useful in the present invention are curcumin which is the major pigment in turmeric, the coloured oleoresin extract of the Curcuma root, vegetable carbon black, which is produced by fully carbonizing vegetable material and grinding it to a fine powder, and the porphyrin pigments such as oil-soluble chlorophylls based substantially on phaeophytin a or b and epimers and isomers hereof.

In accordance with the invention the natural pigments in the above compositions are present in the form of bodies of an average size which is at the most 10 µm. Preferably, the pigment is in the form of bodies having an average size of at the most 5 µm, preferably at the most 2 µm and more preferably at the most 1 µm. It is contemplated that the ability of the pigment to provide an attractive colour hue and to provide an effective colouring e.g. when the composition is used in coating compositions, is increasing with decreasing size of the pigment bodies.

In specific embodiments of the invention, the pigment bodies are solid particles such as e.g. of curcumin, β-carotene or carbon black whereas in other embodiments, the pigment bodies are droplets of an oleoresin pigment including as examples, a paprika oleoresin or turmeric oleoresin. In specific embodiments, a pigment is incorporated into the aqueous dispersion in the form of droplets consisting of a solution or a dispersion, such as an emulsion of the pigment, e.g. in a food grade or pharmaceutically acceptable vegetable oil. Such a dispersion may further contain a food grade emulsifying agent including as examples a lecithin or a monoglyceride emulsifying compound.

As mentioned above, the natural pigment-containing bodies are dispersed in an aqueous phase comprising a hydrocolloid and the dispersion is provided without the addition of surface active substances such as an emulsifying agent or a surfactant. For the purposes of the present invention suitable hydrocolloids include: an animal or vegetable protein such as gelatin which can be derived from mammals or fish, milk protein or soy protein, an exudate such as gum arabic, tragacanth and other gums such as guar gum, locust bean gum or xanthan gum, agar, alginate, carrageenan, furcelleran, pectin, cereal flours and starches, starch derivatives, microcrystalline cellulose, cellulose derivatives such as carboxymethyl cellulose, dextran, and synthetic hydrocolloids including as an example polyvinylpyrrolidone. Presently preferred hydrocolloids are gelatin and gum arabic. The hydrocolloid may also be a mixture of hydrocolloids.

It is contemplated that the hydrocolloid acts as a protective colloid, that it prevents agglomeration of the pigment bodies and that it provides wetting and dispersing activity.

The hydrocolloid is suitably used in an amount in the range of 1–90% by weight of the natural pigment, such as in the range of 2–80% by weight. In preferred embodiments, the amount of hydrocolloid is in the range of 3–60% by weight such as in the range of 5–50% by weight and e.g the amount of hydrocolloid can be less than 10% by weight of the natural pigment. In other preferred embodiments, the amount of hydrocolloid is more than 100% by weight of the natural pigment, such as more than 200% by weight and e.g. more than 300% by weight of the natural pigment.

The amount of pigment may also be calculated on the composition. Thus, the amount of hydrocolloid is preferably in the range of 1–50% by weight of the composition, preferably in the range of 5–40% by weight, such as in the range of 10–25% by weight.

In accordance with the invention, the composition contains at least 5% by weight of water such as in excess of 10% by weight. One advantage of the composition according to the invention is the possibility of providing it with a water content within a wide range whereby the composition can be adapted to particular customer demands. A composition with a low content of water will appear as a viscous paste. Depending on the natural pigment, a composition having a water content in the range of 5–40% by weight will typically appear as a paste, a gel or a viscous liquid. With an increasing water content above this level, the consistency of the composition will acquire an increasingly lower viscosity and become liquid. It is contemplated that a concentrated pasty composition will be advantageous from a user point of view, since it can easily be transported and stored and furthermore, the natural pigment will be protected well against light and oxidation in such a concentrate. It is evident that a concentrated composition according to the invention can be diluted with water to any desired pigment concentration.

The selection of a suitable amount of the natural pigment in the composition according to the invention is based on the particular type of pigment and the particular intended application for the composition and a wide range of the amount of pigment is therefore contemplated such as a range of 0.5–90% by weight of the dispersion, although amounts in excess of this range is envisaged. In preferred embodiments, the amount of pigment is in the range of 1–50% by weight, and may more preferably be in the range of 5–40% by weight. Based on the dispersed phase a useful amount is in the range of 10 to 30% by weight, including about 20% by weight of the dispersion. In specific embodiments of the invention the natural pigment of the composition comprises a mixture of two or more natural pigments.

In accordance with the invention, the aqueous phase of the composition can as a further component comprise a carbohydrate or a sugar alcohol or a mixture hereof. The carbohydrate is preferably selected from a monosaccharide, a disaccharide or an oligosaccharide including as examples glucose, lactose, fructose, sucrose. The sugar alcohol can e.g. be selected from sorbitol, mannitol, dulcitol, adonitol or sorbitol. The amount of the sugar alcohol is preferably in the range of 0–95% by weight of the dispersion, such as 5–50% by weight including the range of 10–30% by weight.

In useful embodiments, the composition according to the invention is a coating composition comprising the above dispersion of a water-insoluble and/or hydrophobic natural pigment and at least one further ingredient which is normally used in a composition for colouring coating layers of e.g. a tablet, a dragee, a pill or a capsule. Such further ingredients can be selected from additional sugar to provide a syrup, a plasticizing agent such as propylene glycol, a film coating resin, a stabilizing agent, a further colouring agent such as $CaCO_3$ or titanium dioxide, or a lower alcohol. The composition may also be a composition intended for decoration purposes such as a glazing composition or a "printing" composition.

As it is mentioned above, the composition according to the invention is useful as a colouring agent for food products. Any food product comprising an aqueous phase wherein the composition is dispersible can be coloured. Thus, the composition is suitable for colouring of liquid food products including soft drinks, carbonated beverage products and milk products. The latter products include not only sweet milk products but also acidified milk products such as yogurt.

An interesting application of the composition according to the invention is the colouring of edible products being manufactured by extrusion, e.g. edible film for containing a food product such as a meat product. A typical example hereof is collagen films used as casings for sausage products. An effective amount of the colouring composition is added to the aqueous mixture to be extruded or casted and the resulting edible film will contain the colour pigments. It has been found that the natural pigments when incorporated in such extruded edible films in contrast to known food colours do not migrate into the contained food product and furthermore, the pigment is not released into water in which the products are cooked.

Other examples of extruded products where the pigment compositions according to the invention are useful include breakfast cereals, cakes, bread, snacks, confectionary products, breadings, crisps and grains. It has been found that the fact that the compositions do not contain any lipids or surface active substances make them particularly useful in the manufacturing of expanded products made by an extrusion process, since the expansion in such processes is lower when lipids and/or surface active substances are added to the extrusion mixture.

A further advantageous use of the compositions is the colouring of confectionary products including as examples candies, acid drops and jelly products since the pigments in the compositions according to the invention are acid stable.

Several food products such as e.g. soft drinks, juices, soups and sauces are manufactured as initially liquid products which are subsequently dehydrated to a dry, storage stable product typically having a water content of at the most 10% by weight. The compositions according to the invention are also useful for the colouring of such products in that the colouring of the products after rehydration will substantially be of the same strength and hue as the starting liquid food product.

As it is mentioned above, it is a well known problem in the food industry that colouring agents used in food products tend to migrate within the food product or into the environment of the product. This phenomenon is also in the art referred to as "bleeding". This problem is particularly troublesome if it occurs in food products which comprise multiple, separated compartments or layers where the colouring agent is not added to all of such compartments, but only to one or more selected compartments. A colouring agent which, do not migrate in such products are therefore highly desirable in the industry. It has been found that the pigments of the compositions according to the invention are retained in the compartment(s) to which they have been added and do not migrate into adjacent non-coloured compartments.

One typical example of such a compartmentalized or layered food product is dessert products, which optionally are acidulated, comprising at least one layer of fruit filling to which a colouring agent is added, and one or more layers of other ingredients also having an aqueous phase but to which a colouring agent is not added. Another example of such a product is a layered cake. It is evident that migration of colouring agent into the non-coloured layers result in a highly unacceptable appearance of these layered products. As it is shown in the below examples, the compositions according to the invention can be used in such products without giving rise to "bleeding" problems. A further example of a product where it is advantageous to avoid migration of pigments is a cereal breakfast product to be eaten with milk.

Avoidance of pigment migration is also critical in connection with edible products comprising a surface decoration layer in which a colouring agent is dispersed. Clearly, it is undesirable if the added pigment migrates from the decoration layer into the subjacent product layer. Typical examples of surface decorated products are meat products such as surimi and other delicatessen products where the decoration e.g. may be in the form of a water-based gel which is coloured with the pigment composition while liquid and subsequently applied on the product to solidify. Other examples of surface decorated products are bakery product having sugar icing (glazing) on top or coloured decoration particles. When added to such decoration layers or particles, the pigments in the compositions according to the invention do not migrate from the layers or particles.

Dragees constitute a particular type of edible multilayered products where one or more coating layers typically consisting of sugar are applied onto a center of an edible ingredient. Examples of such centers to be coated include chewing gum, sugar granulates, sugar tablets and chocolate. Colouring of such edible centers is typically carried out in one or more panning steps where the centers are coated with a sugar syrup containing the colouring agent. Normally, it is required to apply several coating layers to obtain a sufficient covering with colour. With known water soluble or dispersible colouring agents based on lakes it is frequently required to apply 20 coating layers or more. It has been found that the compositions according to the invention are highly suitable for such coating purposes and that dragees with a sufficient colouring can be obtained by applying less than 20 layers, such as 2–15 layers. Furthermore, it has been found that the natural pigments of the compositions as contained in coating layers do not come off on fingers on handling or on mucosal surfaces when the dragees are consumed.

A highly attractive characteristic of the compositions according to the invention is that they are useful as colouring agents in the manufacturing of a pharmaceutical product. Thus, the compositions can be used for colouring of pharmaceutical products comprising multiple, separated compartments essentially in the same manner and with the same advantages as described above for compartmentalized food products. In particular, the compositions according to the invention are useful for colouring of compositions for conventional film-coating of tablet, pills or granules containing pharmaceutically active substances.

For such coating purposes the water dispersible composition according to the invention is typically added to a sugar syrup suspension, e.g. using sucrose. The solids content of such a coating syrup is normally in the range of 60–80% by weight. The amount of the natural pigment composition which is added to the coating syrup is generally in the range of ½–50% by weight of the syrup. The thus coloured coating mixture may contain further components such as stabilizers, preservatives, viscosity modifying agents and plasticizers.

The pharmaceutical centers are coated repeatedly in a conventional panning process and the number of repeated coatings required depends on the particular pigment and the desired appearance of the finished product. However, with the composition according to the invention, relatively few coating layers are required to obtain an attractive colouring. Thus, less than 20 layers is normally required and in most cases, 5–15 layer will suffice.

In addition to the above applications of the compositions, it is contemplated that they are also useful for colouring of pharmaceutical products in liquid form such as solutions, suspensions or dispersion having an aqueous phase.

As mentioned above, the present invention provides in one aspect a method of preparing the ready-to-use water dispersible pigment composition according to the invention. In a first step of the method a dispersion of a water-insoluble and/or hydrophobic natural pigment is prepared by comminuting the pigment in an aqueous phase. This comminution step is carried out without the addition of surface active substances such as emulsifying compounds, but in the presence of a hydrocolloid of a type and in amounts as mentioned above. The comminution can be obtained by any conventional technique which will result in comminution of a solid or an oil into discrete bodies having a size of at the most 10 $\mu$m. However, it may be advantageous to continue the comminution until the pigment is in the form of bodies having an average size of at the most 5 $\mu$m, preferably at the most 2 $\mu$m and more preferably at the most 1 $\mu$m.

Applicable comminution techniques include milling and homogenization as it is described in details in the below examples. In a useful embodiment, the amount of hydrocolloid is less than 10% by weight of the pigment.

The above comminution step may be repeated one or more times in order to obtain the required body size. The dispersion may be carried out in at least two steps of which the first step is a milling in an aqueous phase comprising less than 10% by weight of hydrocolloid, followed by further homogenizing the dispersion, optionally with the addition of a further amount of hydrocolloid.

As mentioned above, the natural pigments may either be in the form of solid particles or in the form of an oleoresin such as a paprika oleoresin. Furthermore, a pigment such as an oleoresin pigment can be used in the method according to the invention in the form of a dispersion of the pigment in a food grade and pharmaceutically acceptable oil such a vegetable oil.

It will be understood that the method may also comprise the preparation of a pigment dispersion in which a mixture of water-insoluble and/or hydrophobic natural pigments is used. In this manner pigment compositions having a particular attractive colour tone can be provided as a result of the combination of two or more pigments having differing colours.

As also mentioned above, the method may comprise the addition of carbohydrate to the aqueous phase either before or after the comminution or it may comprise adding to the dispersion of the water-insoluble and/or hydrophobic natural pigment at least one further ingredient. Such further ingredients may e.g. be selected from antioxidants, stabilizing agents, plasticizers, viscosity modifying agents, alcohols, resins and preservative agents.

EXAMPLE 1

Preparation of Paprika Oleoresin Composition 8.0 kg gelatin (dry weight) was added slowly to 16.5 kg demineralised water at about 65° C. with stirring until the gelatin was dissolved. 15.0 kg of sucrose was added and the mixture was agitated using a mixer until the sugar was dissolved. 10.6 kg of paprika oleoresin was heated to 40–45° C. and added to the above solution using a high speed mixer with a homogenising head and the mixture homogenised at maximum velocity for about 30 minutes. The mixing was continued until a homogeneous mixture was obtained (about 20 minutes) at high speed. The temperature was then raised to about 70° C. and agitation continued for about 10 minutes at low speed resulting in a homogenous water dispersible pigment composition. The composition has a water content of about 33% by weight.

Working Instruction 1

Preparation of Paprika Oleoresin Compositions with Different Water Contents Compositions with varying water content can be prepared using the method as described in Example 1 with the following ingredients (in kg):

|   | Water content | Gelatin | Demineralised water | Sucrose |
|---|---|---|---|---|
| A | 25% | 8.0 | 12.5 | 19.0 |
| B | 30% | 10.0 | 15.0 | 14.5 |
| C | 33% | 12.0 | 16.5 | 11.0 |
| D | 40% | 15.0 | 20.0 | 4.4 |

Keeping the amount of pigment constant at 10.6 kg in the four compositions will result in the following gelatine contents calculated by weight of the pigment:

A: 75%, B: 94%, C: 113% and D: 142% respectively.

Working Instruction 2

Preparation of Chlorophyll Oleoresin Compositions

The above paprika oleoresin compositions can be prepared using the method and ingredients of Example 1 and Working Instruction 1 wherein paprika oleoresin is replaced by the same amount of chlorophyll oleoresin.

EXAMPLE 2

Preparation of a Paprika Oleoresin Composition Using Homogenization at High Pressure 8.0 kg of gelatin (dry weight) was added slowly to 15.0 kg demineralised water at a temperature of about 65° C. with agitation until the gelatin was dissolved. 16.5 kg of sucrose was added under agitation until the sucrose was dissolved. 10.6 kg of paprika oleoresin was heated to 40–45° C. and added to the above mixture under agitation using a high speed mixer with a homogenization head and the mixture homogenised/mixed at high velocity over a short period. The product was passed through a homogeniser at high pressure (12.000–30.000 psi) resulting in a homogeneous water dispersible pigment composition. The resulting composition has a water content of about 30% by weight.

EXAMPLE 3

Preparation of a Bixin Composition 8.0 kg gelatin (dry weight) was added slowly to 16.5 kg demineralised water at a temperature of about 65° C. with stirring until the gelatin was dissolved. 15.0 kg of sucrose was added under agitation until the sugar was dissolved. 10.5 kg of bixin powder was added to the above mixture under agitation using a mechanical stirrer. Mixing was continued until a homogeneous mixture was obtained.

The mixture was milled using a suitable mill until a stable dispersion of the pigment was obtained. The milled product was heated under gentle agitation to about 75° C. and kept at this temperature for about 10 minutes. The resulting composition has a water content of about 33% by weight.

Working Instruction 3

Preparation of Bixin Compositions with Different Water Contents

Bixin compositions with varying contents of water, gelatin and sucrose can be prepared using the method as described in Example 3 with the following ingredients (in kg):

|   | Water content | Gelatin | Demineralised water | Sucrose |
|---|---|---|---|---|
| A | 25% | 8.0 | 12.5 | 19.0 |
| B | 30% | 10 | 15.0 | 14.5 |
| C | 33% | 12.0 | 16.5 | 11.0 |
| D | 40% | 15.0 | 20.0 | 3.4 |

The resulting compositions will have the following gelatin contents calculated by weight og the pigment:

A: 76%, B: 95%, C: 114% and D: 142% respectively.

EXAMPLE 4

Preparation of Turmeric Composition

A turmeric composition was prepared using the same method and amounts of ingredients as described in Example 3, but with substitution of bixin powder with the same amount of curcumin powder.

Working Instruction 4

Preparation of Turmeric Composition Using Gum Arabic as Hydrocolloid

The composition can be prepared using the method and ingredients as described in Example 4 wherein gelatin is replaced by the same amount of gum arabic.

EXAMPLE 5

Comparative Study of Migration in an Acidulated Dessert Coloured with Pigment Compositions According to the Invention and Reference Colouring Agents Mashed apple was mixed with the below amount of colouring agents and 25 ml glass containers were filled half with the mixtures, the remaining half of the containers were filled with yogurt. The container were kept at 5° C. and the migration of the colour into the yogurt layer in cm was recorded after 4, 7, 11 and 28 days.

All the reference colouring agents were products of Chr. Hansen A/S, Hørsholm, Denmark. The following agents were tested (dosages in g colouring agent/g mashed apple):

T-PT8-WS: turmeric dissolved in polysorbate 80 (0.068),

P-50,000-WS: paprika oleoresin dissolved in polysorbate 80 (0.067),

Paprika oleoresin composition of Example 1 (0.131),

Bixin composition of Example 3 (0.029),

Turmeric composition of Example 4 (0.092)

TABLE 5.1

Migration of test compositions and reference colouring agents in cm

|  | Days | | | | |
| --- | --- | --- | --- | --- | --- |
|  | 1 | 4 | 7 | 11 | 28 |
| Bixin, test |  | 0 | 0 | 0 |  |
| Turmeric, reference | 0.5 |  |  |  |  |
| Turmeric, test | 0 |  |  |  |  |
| Paprika, reference | 0.5 |  |  |  |  |
| Paprika, test | 0 |  |  |  |  |

These results clearly shows that migration did not occur with the natural pigment compositions according to the invention, whereas the reference products containing the corresponding pigments in solution migrated to a significant extent.

EXAMPLE 6

Coating of Confectionary Using Coating Syrups Containing Natural Pigment Compositions A coating syrup was prepared from 3.5 kg sucrose and 1.5 kg water by mixing and heating to 80° C. under agitation with a propel stirrer. The syrup was cooled to 50° C. and 270 g of a natural pigment composition according to the invention containing about 200% of pigment was added to the syrup. Two coloured coating syrups containing pigment compositions with turmeric or bixin, respectively were prepared in this manner. The concentration of the natural pigments in the syrups was about 0.4% of the syrup dry matter.

4–5 kg confectionary centers with a diameter of 17 mm and with a sugar coating containing $TiO_2$ were used to test the colouring ability of the coating syrups.

In both experiments, a satisfactory colour of the resulting dragees was obtained even with 3–4 layers of coloured syrup and a strong and dark colour was obtained after 10 layers of coating.

The experiment illustrated that the natural pigment compositions dispersed very well without the use of a high speed mixer.

The colouring ability was high in that good colouring was seen after only 3–4 layers without the addition of gum arabic which is often used in coating syrups to enhance the adherence of the colouring agent. It was observed that no colouring of teeth, mouth or hands occurred on eating the coloured dragees.

EXAMPLE 7

The Performance of Pigment Compositions in Soft Drink

A concentrated soft drink medium was prepared with the following composition:

| | |
| --- | --- |
| Sucrose | 430.0 g |
| Na-benzoate, food grade | 0.7 g |
| K-sorbate, food grade | 0.9 g |
| Ascorbic acid | 0.1 g |
| Citric acid monohydrate, food grade | 8.6 g |
| Demineralised water, | ad 1000.0 g |

The concentrate was diluted 1:4 before use with demineralised water. The diluted soft drink medium had a pH of 3.0±0.2.

Pigment compositions as prepared in Examples 1, 3 and 4, respectively (Test-Paprika, Test-Annatto and Test-Turmeric), were added as test samples to the diluted medium at the following pigment concentrations, respectively: 10 units, 20 ppm, and 28 ppm. The following colouring agents containing the corresponding pigments were added to the soft drink medium as reference samples:

P-50,00-WS, paprika oleoresin in polysorbate 80 (10 units),

A-720-WS-AP, norbixin in propylene glycol, polysorbate, $Ca(OH)_2$ and water (20 ppm), T-PT8-WS, turmeric in polysorbate 80 (30 ppm).

L*a*b* values were measured using a Minolta Tristimulus CT-210 equipped with a D65 lamp in a 1 cm cuvette. The measurements were made after dissolution/dispersing of the colours and after storage for 8 weeks in the light and dark, respectively. ΔE expresses the difference in colour parameters. The results are summarized in the below table:

TABLE 7.1

Transparency of soft drink medium and ΔE at day 0 and after storage for 8 weeks

| Colouring agent | Transparency | ΔE, daylight | ΔE, dark |
| --- | --- | --- | --- |
| Test-Paprika | Cloudy | 45 | 17 |
| P-50,000-WS | Transparent | 43 | 35 |
| Test-Annatto | Cloudy | 13 | 5 |
| A-720-WS-AP | Transparent | 48 | 35 |
| Test-Turmeric | Cloudy | 4 | 3 |
| T-PT8-WS | Transparent | 94 | 33 |

These results illustrate that the compositions according to the invention has a high stability as compared to the reference colouring agents. Furthermore, the water dispersible compositions of the invention confer to the soft drink medium a cloudy appearance whereas the reference soft drink samples remained transparent. A cloudy appearance of a soft drink is a highly desirable characteristic of a coloured soft drink.

EXAMPLE 8

Light Stability of Turmeric Pigment Composition

A sugar glazing was prepared consisting of 300 g icing sugar and 30 g of water. To this mixture was added a composition according to the invention at a concentration of 40 and 80 ppm of turmeric (Test-Turmeric). As a reference, T-PT8-WS (turmeric solubilized in polysorbate) was added to glazing at the concentrations 10, 20 and 40 ppm of the pigment. The stability of the pigment in the two compositions was determined by measuring the chroma immediately after addition of pigment and after 1 day in daylight.

The results are summarized in the below table:

TABLE 7.1

Stability of colour as changes in chroma during storage in daylight for 1 day

| Composition | ppm pigment | chroma, initial | chroma, after 1 day |
|---|---|---|---|
| Test-Turmeric | 80 | 46 | 47 |
| Test-Turmeric | 40 | 36 | 33 |
| T-PT8-WS | 80 | 75 | 58 |
| T-PT8-WS | 40 | 68 | 47 |
| T-PT8-WS | 20 | 58 | 36 |
| T-PT8-WS | 10 | 47 | 26 |

It was thus clearly demonstrated that the pigment compositions according to the invention has a significantly higher stability against daylight than the reference compositions.

EXAMPLE 9

Preparation of a Bixin Composition with Dispersion of Bixin in Two Steps 1.0 kg of gelatin (dry weight) was added slowly to 16.0 kg demineralised water at a temperature of about 65° C. with agitation until the gelatin was dissolved. 15.5 kg of sucrose was added under agitation until the sugar was dissolved. 10.5 kg of bixin was added to the above mixture under agitation using a mechanical stirrer. Mixing was continued until a homogeneous mixture was obtained. The mixture was milled using a suitable mill until a stable dispersion of the pigment was obtained. The milled product was heated under gentle agitation to about 70° C., 7.0 kg of gelatine was added and dissolved using agitation. The temperature was kept at this temperature for about 10 minutes. The resulting composition has a water content of about 32% by weight.

What is claimed is:

1. A ready-to-use water dispersible pigment composition that contains in excess of 10% by weight of water, the composition comprising a dispersion of a water-insoluble and/or hydrophobic natural pigment in the form of bodies of an average size which is at the most 10 µm, said bodies being dispersed in the absence of a surface active substance in an aqueous phase comprising a hydrocolloid in an amount of at least 1% by weight of the pigment, the composition, when it is added to a food product or a pharmaceutical product comprising multiple, separated compartments, whereby the composition is dispersed in one or more selected compartments, essentially does not migrate from said compartment(s) where it is dispersed into other compartments.

2. A composition according to claim 1 wherein the natural pigment is selected from the group consisting of a carotenoid, curcumin, a porphyrin pigment and vegetable carbon black.

3. A composition according to claim 1 wherein the pigment bodies are selected from the group consisting of droplets of an oleoresin pigment and droplets of a dispersion of a pigment.

4. A composition according to claim 3 wherein the hydrocolloid is selected from the group consisting of a protein, agar, alginate, carrageenan, furcelleran, pectin, a starch, a starch derivative, microcrystalline cellulose, a cellulose derivative, dextran and a synthetic hydrocolloid.

5. A composition according to claim 1 wherein the aqueous phase further comprises a carbohydrate.

6. A composition according to claim 1 wherein the hydrocolloid is selected from the group consisting of a protein, a polysaccharide and a gum selected from the group consisting of guar gum, locust bean gum, xanthan gum, tragacanth gum and gum arabic.

7. A coating composition comprising a composition according to claim 1 and at least one further ingredient selected from the group consisting of a syrup, a plasticizing agent, a film coating resin, a stabilizing agent, a further colouring scent and a lower alcohol.

8. An edible product comprising a composition according to claim 1.

9. A edible product according to claim 8, comprising multiple, separated compartments such that the composition is dispersed in one or more selected compartments, and the composition in one compartment essentially not migrating to other compartments.

10. A pharmaceutical product comprising a composition according to claim 1.

11. A method of preparing a water dispersible pigment composition according to claim 1, said method comprising preparing a dispersion of a water-insoluble and/or hydrophobic natural pigment by comminuting the pigment in the absence of an emulsifying agent in an aqueous phase containing a hydrocolloid in an amount of at least 1% by weight of the pigment to obtain a dispersion containing the pigment in the form of bodies having an average size of at the most 10 µm, the composition containing in excess of 10% by weight of water.

12. A method according to claim 11 wherein the pigment is a solid pigment.

13. A method according to claim 11 wherein the pigment is dispersed in at least two steps.

14. A method according to claim 13 wherein the first step is a milling in an aqueous phase comprising less than 10% by weight of hydrocolloid, followed by further homogenizing the dispersion, optionally with the addition of a further amount of hydrocolloid.

15. A method according to claim 11 wherein the pigment bodies are selected from the group consisting of droplets of an oleoresin pigment and droplets of a dispersion of a pigment.

16. A method according to claim 15 wherein the hydrocolloid is selected from the group consisting of a protein, agar, alginate, carrageenan, furcelleran, pectin, a starch, a starch derivative, microcrystalline cellulose, a cellulose derivative, dextran, a synthetic hydrocolloid and a gum selected of the group consisting of guar gum, locust bean gum, xanthan gum, tragacanth gum and gum arabic.

17. A method for administering a ready-to-use water dispersible pigment composition comprising dispersing a water dispersible pigment in the aqueous phase of an edible product, wherein said dispersible pigment contains in excess of 10% by weight of water, and comprises a dispersion of a water-insoluble and/or hydrophobic natural pigment in the form of bodies of an average size which is at the most 10 µm, said bodies being dispersed in the absence of a surface active substance in an aqueous phase comprising a hydrocolloid in an amount of at least 1% by weight of the pigment.

18. The method according to claim 17 wherein the edible product is manufactured by extrusion.

19. A method for manufacturing a pharmaceutical product comprising, dispersing a ready-to-use water dispersible pigment, in the absence of a surface active substance, into an aqueous phase of said pharmaceutical product, wherein said ready-to-use water dispersible pigment contains in excess of 10% by weight of water, wherein the ready-to-use water dispersible pigment comprises a dispersion of a water-insoluble and/or hydrophobic natural pigment in the form of bodies of an average size which is at the most 10 µm, wherein said bodies are dispersed, in the absence of a surface active substance, and wherein said aqueous phase comprises a hydrocolloid in an amount of at least 1% by weight of the pigment.

20. The method according to claim 19 wherein the pharmaceutical product comprises multiple, separated compartments whereby the composition is dispersed in one or more selected compartments, the compositions in one compartment essentially not migrating to other compartments.

* * * * *